(12) United States Patent
Huff

(10) Patent No.: US 6,711,938 B2
(45) Date of Patent: Mar. 30, 2004

(54) NON-DESTRUCTIVE JOINT SEALANT TESTING DEVICE

(76) Inventor: Daniel N. Huff, 19153 Shoshone Rd., Bend, OR (US) 97702

( * ) Notice: Subject to any disclaimer, the term of this patent is extended or adjusted under 35 U.S.C. 154(b) by 0 days.

(21) Appl. No.: 10/208,260

(22) Filed: Jul. 29, 2002

(65) Prior Publication Data

US 2003/0037595 A1 Feb. 27, 2003

Related U.S. Application Data

(60) Provisional application No. 60/308,897, filed on Jul. 30, 2001.

(51) Int. Cl.[7] .................................................. G01M 3/02
(52) U.S. Cl. ........................................................... 73/37
(58) Field of Search .............................. 73/37, 168, 40, 73/49.2, 49.5, 49.8, 788, 865.5, 865.9

(56) References Cited

U.S. PATENT DOCUMENTS

| | | | |
|---|---|---|---|
| 4,043,179 A | 8/1977 | Ingle, Jr. ........................ | 73/37 |
| 5,078,005 A | 1/1992 | Krempel et al. ................ | 73/37 |

(List continued on next page.)

OTHER PUBLICATIONS

"Standard Terminology of Building Seals and Sealants", ASTM Designation: C 717–88c, American Society For Testing And Materials, pp. 1–3, 1988 (no month).
Standard Test Method for Adhesion and Cohesion of Elastomeric Joint sealants Under Cyclic Movement (Hockman Cycle), ASTM Designation: C 719–93, American Society For Testing And Materials, p.104109, Jan. 1994.
Section V Sealants—"Testing Sealants: Specifiction That Waterproofing Contractors Need To Know", *BRM Update*, pp. 1–5, Feb. 1994.
"Standard Specification for Elastomeric Joint Sealants", ASTM Designation: C 920–95, American Society For Testing And Materials, 3 pp., 1995 (no month).
"Standard Guide for Use of Joint Sealants", ASTM Designation: C 1193–91 (Reapproved 1995), pp. 279–287, 1995 (no month).
"Standard Test Method for Structural Performance Of Exterior Windows, Curtain Walls, And Doors By Uniform Static Air Pressure Difference", ASTM E 330–79, American Society For Testing And Materials, pp. 108, 1979 (no month).
"Standard Test Method for Field Determination Of Water Penetration Of Installed Exterior Windows, Curtain Walls, And Doors By Uniform Or Cyclic Static Air Pressure Difference", ASTM Designation: E 1105–86, pp. 1–6, 1986 (no month).
*Weatherproofing Sealant Guide*, Dow Corning, 35 pages, Oct. 1994.
"Proposed Recommended Practice for Evaluating Adhesion of Installed Weatherproofing Sealant Joints".

*Primary Examiner*—Helen Kwok
*Assistant Examiner*—Jay L. Politzer

(57) ABSTRACT

A device for determining the adequacy of a sealant between construction elements is attached to a source of compressed air whose pressure is controlled by a regulator. The device includes a cylinder containing at least one piston, the piston containing an air chamber and a plunger, the air chamber being in communication with a pressure gauge. The device also includes an armature having a first and a second end, the first end being attached to the cylinder, the second end having a flow valve and an air fitting in communication with the air source, the handle containing tubing as a means to conduct air from the compressed air source, the tubing being interrupted with a bleed valve. The device also includes a moveable tip such that the tip moves in the direction parallel to the axis of the cylinder, said tip comprising a wheel, a wheel bracket and a plunger shaft, the plunger shaft being attached to the plunger within the piston. In use, the operator holds the device so that the moveable tip presses against the sealant with constant pressure.

5 Claims, 16 Drawing Sheets

U.S. PATENT DOCUMENTS

| | | | |
|---|---|---|---|
| 5,127,260 A | 7/1992 | Robertson | 73/37 |
| 5,315,861 A | 5/1994 | Egan et al. | 73/37 |
| 5,351,562 A | 10/1994 | Scott | 73/37 |
| 5,454,260 A | 10/1995 | Wang | 73/150 A |
| 5,705,736 A | 1/1998 | McCranie | 73/37 |
| 5,744,703 A | 4/1998 | Krenceski et al. | 73/54.01 |
| 6,513,369 B1 * | 2/2003 | Chew | 73/81 |

\* cited by examiner

NON-DESTRUCTIVE JOINT SEALANT TESTING DEVICE

CROSS REFERENCE TO RELATED APPLICATION

This application claims priority to provisional application No. 60/308,897, filed Jul. 30, 2001, incorporated herein by reference to the extent not inconsistent herewith.

BACKGROUND OF THE INVENTION

1. Technical Field

This invention is in the field of building construction and more particularly testing of construction elastomeric sealants and a device therefor.

2. The Prior Art

Large modern buildings are often constructed with exterior design elements (a curtain wall), such as plate glass panels or aluminum-clad window, pre-cast concrete panels, etc. The curtain wall protects from the outside weather and bears no load. The curtain wall "floats" on the superstructure of the building. On a single building one may see brick, concrete, stone and other materials, each as a horizontal ribbon interspersed with ribbons of glass. Each element is independently attached to the building and supports no other element. The exterior of the building is in effect a mosaic of different elements. Each element must have the ability to move independently of the others to allow for thermal changes, wind load and seismic movements.

These elements are connected by elastomeric sealants, which also serve to waterproof the building. The sealant is applied as a viscous liquid, which cures to a durable, flexible rubber. On most buildings that employ the curtain-wall design, the sealant becomes the only barrier between the outside and inside of the building. Although the sealant appears to be a minor part of the overall construction, it is of extraordinary importance to the performance of the building skin. Adhesion of the sealant to the elements may be adversely affected by moisture in or on the substrate during sealant application and cure, contaminated or weak surfaces, and poor application technique. Failure of the seal results in water entry, which if left unchecked, causes mold to grow. This is often the source of "sick building syndrome." Failure of the seal also permits air passage. It has been estimated that as much as 40% of heating and cooling costs are due to unplanned entry of air through cracks and holes in a building's sealant.

Other uses of elastomeric joint sealants include the following. Silicone structural glazing (SSG) comprises gluing glass lites to interior mullions on the vertical jambs (two-sided SSG) and/or also on the horizontal head and sill (4-sided SSG). "Tilt-up" style construction uses Portland Cement Concrete to create panels where the movement joints between the panels are sealed. Elastomeric movement joints are used in horizontal pavement such as in parking structures, airplane runways, bridges, etc.

A number of methods have been used to test the adequacy of elastomeric seals. ASTM C 1193—Standard Guide for Use of Joint Sealants describes the use of single and multi-component, cold-applied joint sealants for parallel joint sealing applications. ASTM C 920—Standard Specification for Elastomeric Joint Sealants covers the properties of a cured single- or multi-component cold-applied elastomeric joint for sealing, caulking or glazing operations. ASTM C 719—Standard Test Method for Adhesion and Cohesion of Elastomeric Joint Sealants Under Cyclic Movement (Hockman Cycle) is an accelerated laboratory procedure for evaluating the performance of a building sealant in a test configuration that is subjected to water immersion, cyclic movement and temperature change. ASTM E 330—Standard Test Method for Structural Performance of Exterior Windows, Curtain Walls, and Doors by Uniform Static Air Pressure Difference covers the determination of the performance of individual exterior elements under uniform static air pressure differences in a test chamber and is intended to represent the effects of various wind loads on exterior elements.

In the field, the current industry standard test for the functionality of sealants is a destructive test called a pull test. The pull test is performed after the sealant has cured, typically two to three weeks after application. First, a short piece of adhesive is cut from a joint by cutting from one side of the joint to the other; then starting at the first cut, two perpendicular cuts approximately 5 cm long are made along the elements. The tester grasps the freed piece of sealant firmly between the fingers and pulls away from the curtain wall at a 90° angle or more and tries to pull the uncut sealant out of the joint. If adhesion is acceptable, the sealant itself tears (a cohesive tear) and leaves sealant attached to the substrate. Failure of the sealant to adhere to the substrate (an adhesive tear) is a test failure. Obviously, whether or not the test is successful, sealant needs to be replaced.

The current industry standard calls for one of these pull tests for every 5 levels per building elevation. For example, on a square, 100-ft by 100-ft, 20-story building, four such 2-inch tests are performed for each side of the building, or a total of 16 2-inch tests in what is perhaps a field of 8,000 linear feet of sealant. In other words, the sample is only 0.003% of the sealant. With this test if the sealant fails, usually a large area of sealant is condemned and replaced.

By way of actual example, an office building had a curtain wall of aluminum windows and architectural concrete panels with both smooth and sandblasted surfaces. The sealant stuck to the smooth concrete and metal and appeared to stick to the sandblasted areas, which was confirmed by a pull test. However, the pull test did not identify the problem of poor adherence to the sandblasted substrate because the metal side of the joint provided sufficient support to pass the pull test.

On another project, the curtain-wall elements included shop-fabricated, four-sided structurally glazed units using a two-part silicone sealant, which was also used to seal the elements. After the elements were installed and cured, a tester applied a strain to the weather seal, randomly using a blunt instrument. Adhesive failure was observed on a regular basis: approximately half of the units failed a modified ASTM E 330 test. Remediation of all sealant was very costly and included removal of all the weather seals, installation of temporary fastening clips, cleaning out the double-sided tape, pumping the structural sealant into the joint, allowing it to cure and finally reinstalling the weather seal. If an efficient non-destructive test had been available, faulty units could have been identified in the shop and only half of the sealant on the building would have required repair.

There is currently no industry standard test method that can provide on-site information as to the adequacy of the sealant without destroying existing joints.

SUMMARY OF THE INVENTION

A device for determining the adequacy of a sealant between construction elements is attached to a source of compressed air whose pressure is controlled by a regulator.

The device includes a cylinder containing at least one piston, the piston containing an air chamber and a plunger, the air chamber being in communication with a pressure gauge. The device also includes an armature having a first and a second end, the first end being attached to the cylinder, the second end having a flow valve and an air fitting in communication with the air source, the handle containing tubing as a means to conduct air from the compressed air source, the tubing being interrupted with a bleed valve. The device also includes a moveable tip such that the tip moves in the direction parallel to the axis of the cylinder, said tip comprising a wheel, a wheel bracket and a plunger shaft, the plunger shaft being attached to the plunger within the piston; In use, the operator holds the device so that the moveable tip presses against the sealant with constant pressure.

In another embodiment, the moveable tip is removable. In yet another embodiment, the pressure gauge is visible when the device is in operation. In yet another embodiment, the handle contains two bleed valves.

In yet another embodiment, there is provided a method of field testing the adequacy of sealant between two adjacent materials which are the same or different. The method includes providing a bead of sealant between two materials; permitting the sealant to cure; providing a device which is capable of exerting a constant pressure on the sealant and for which the pressure can be adjusted; applying the device to the bead at a variety of pressures to establish an optimal pressure to test the sealant in the field; applying the device with the optimal pressure to the sealant in the field; and observing for any separation of the sealant from the materials and any indentation of the sealant.

BRIEF DESCRIPTION OF THE DRAWING FIGURES

DETAILED DESCRIPTION OF A PREFERRED EMBODIMENT

The device is designed to provide a continuous strain to a sealant bead using a roller probe. The pressure that is exerted by the probe is adjustable to a particular sealant and joint width. The device is passed along the length of the bead while the user observes the reaction of the sealant to the strain. Adhesive failures are recorded where they occur.

The device uses a head of air pressure that is maintained across a piston, which has the ability to maintain the prescribed pressure within a stroke using a pressure equalization system. This means that when the probe is engaged to the sealant joint, a constant dialed-up pressure is exerted on the bead. The device is designed to be hand held. Movements of the operator that result in fluctuations within the piston stroke are compensated by the pressure equalization maintained within the device.

The roller probe has a donut-shaped bottom edge to prevent cutting of the sealant. There are various probe widths that are interchangeable, allowing for the appropriate probe width to be chosen for the specific joint width. The goal is to use a probe whose approximate width is one third of the joint width. The device puts an even strain on both sides of the joint because the probe naturally seeks the deeper center of the joint.

The device can be calibrated to any sealant's properties since the device is fully adjustable within the pre-determined pressure. The method used in the calibration of the device, as well as results of this calibration study are described in Example 1.

Additional electronic features may be added to the device. An electronic circuit board is added, which is capable of warning the operator with a light and/or audible tone, which signals that either the device is not engaged to the sealant bead (piston stroke is not activated) or that the device is over-engaged (piston stroke is fully depressed into the device causing overload to the bead). At the top and bottom (or either side) of the wheel assembly end of the device, infrared laser beams are used to determine that the surfaces adjacent to the wheel are equidistant from the device; circuitry could provide the operator with a light and/or audible alarm when the device is out of perpendicularity to the sealant bead by, for example, 10% or more. Another useful feature would be the provision for global positioning and/or laser-guided surveying equipment on the device; this could aid in recording the locations of sealant failure on the structure under review. Another optional but useful feature is incorporation of a video recorder and/or a wireless camera to make a visual recording of the results of sealant testing.

Figure 1:
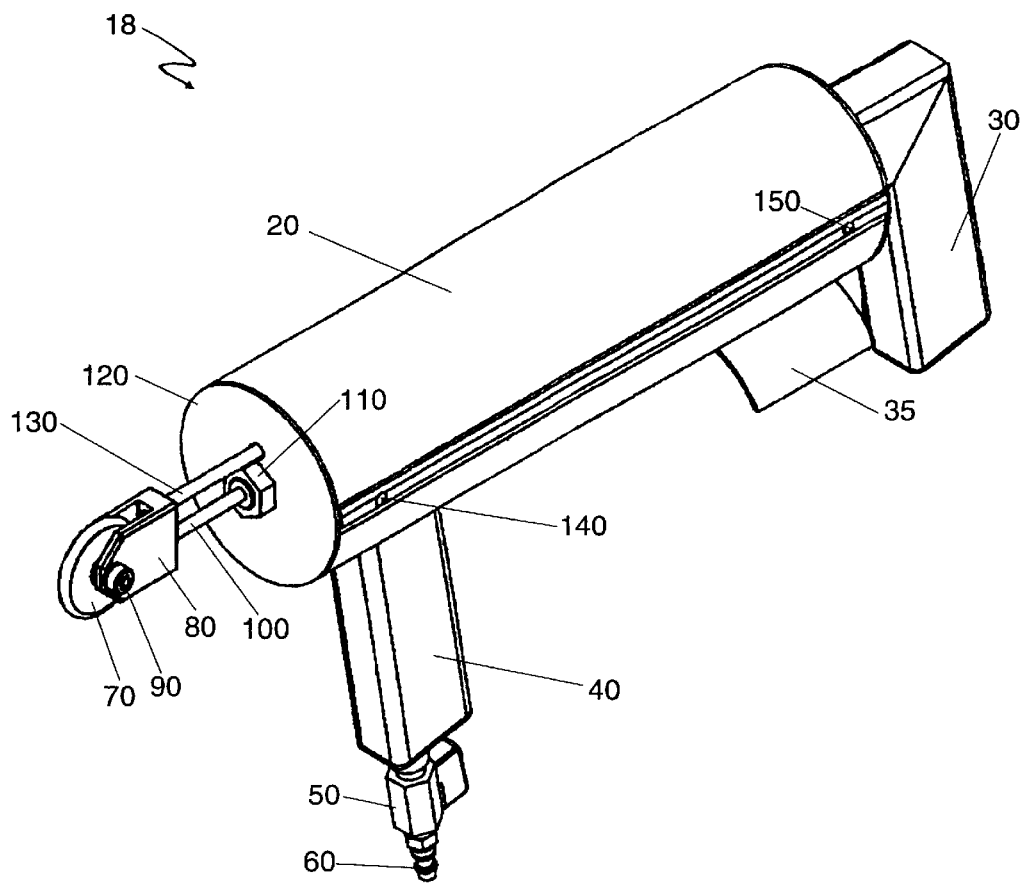
FIG. 1 is a perspective view of the device.

Turning now to one embodiment of the device, FIG. 1 shows a perspective view of the device 18. The device 18 consists of a cylinder 20, a handle 30, a rest plate 35 and an armature 40. Armature 40 is connected (preferably welded) to the cylinder 20 at one end and at the other end to a flow valve 50 and then to an air fitting 60, which in turn connects to a source of compressed gas (not shown). The operative end of the device 18 is wheel 70, which has rounded edges. The wheel 70 is positioned by the wheel bracket 80 and pin 90. The wheel bracket 80 in turn is connected to a movable plunger shaft 100. The plunger shaft 100 moves back and forth into the cylinder 20 through a shaft fitting 110, which is attached to a wheel plate 120. Optionally there can be a stabilizing shaft 130, which also moves back and forth into the cylinder 20 through wheel plate 120, and which prevents rotation of the wheel 70 and the wheel bracket 80. Cylinder 20 is preferably fabricated as two longitudinal halves with a hinge (not shown) and fasteners such as screws 140 and 150. The cylinder 20, handle 30, rest plate 35, armature 40, wheel plate 120 and handle plate (not shown) are made of rigid material, such as metals, including but not limited to steel and aluminum, or rigid plastics. The wheel 70 is a piece of rigid material capable of indenting the sealant material to be tested and capable of having force exerted upon it without deforming. The wheel 70 permits the device to efficiently and non-destructively move along a bead of sealant to permit as much as 100% testing of applied sealant. The wheel assembly can be replaced with a non-rolling rounded cap on the end of the movable plunger shaft 100. Such a device is useful for sampling procedures.

Figure 2:
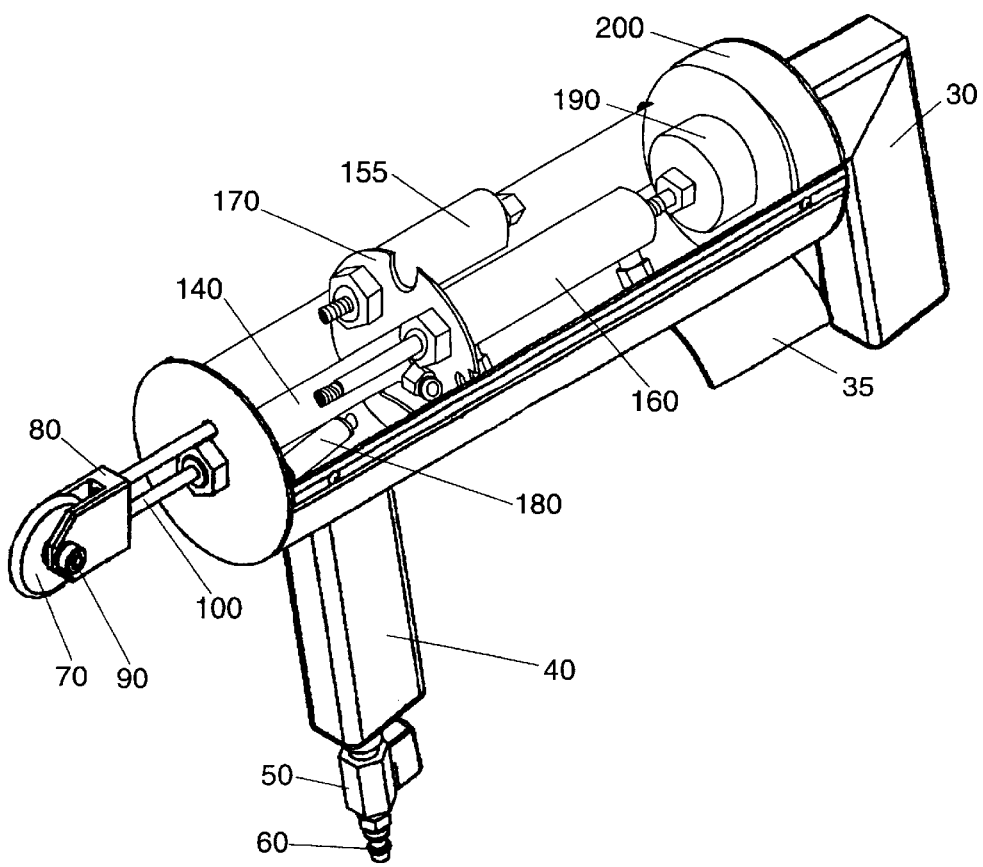
FIG. 2 is a cutaway perspective view of the device.

FIG. 2 is a cutaway perspective view of the device 18 showing the pistons 140, 150 and 160. The number of pistons and their connection can be varied as shown in FIGS. 9–14. The central plate 170 positions the pistons. Also visible in the device is a bleed valve 180 and a pressure gauge 190. It can be seen that the handle 30 attaches to the handle plate 200.

Figure 3:
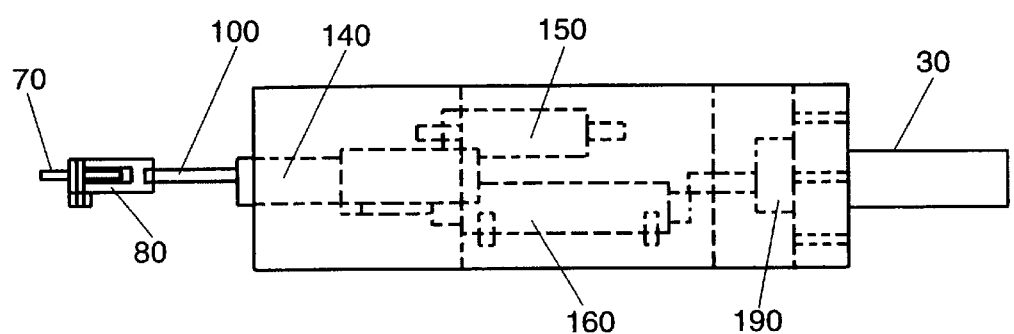
FIG. 3 is a top plan view of the device.

FIG. 3 is a top plan view of the device 18, which shows the arrangement of the pistons 140, 150 and 160. The wheel bracket 80 and the wheel 70 are seen in profile. The wheel 70 is relatively narrow and is replaceable by removing the nut and pin 90. In use, a wheel width is preferably about one-third the width of the bead. Alternately, the wheel assembly (wheel 70 and wheel bracket 80) can be unscrewed from the plunger shaft 100 and replaced with a wheel assembly with a more suitable wheel width.

Figure 4:
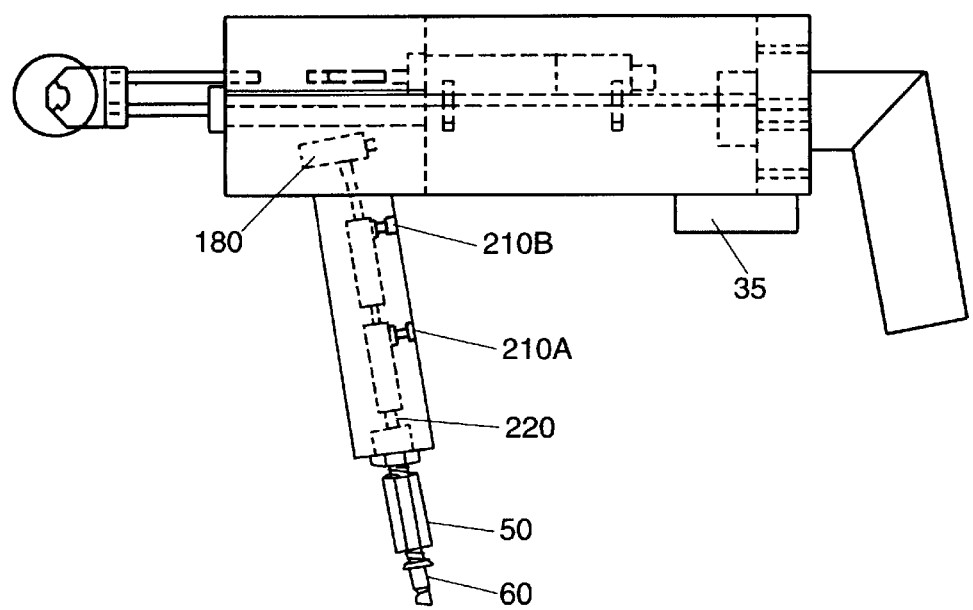
FIG. 4 is a side cross-sectional view of the device.

FIG. 4 is a side cross-sectional view of the device 18, of the cylinder 20 and the armature 40. In the armature can be seen tubing 220 (for the compressed gas) and a first bleed valve 210*a* and a second bleed valve 210*b*. The air pressure within the device is controlled by the regulator for the compressed air source (not shown), the flow valve 50 and the first bleed valve 210*a* and the second bleed valve 210*b*. Although three bleed valves are shown, the only requirement for this embodiment is that there be at least one bleed valve.

Figure 5:
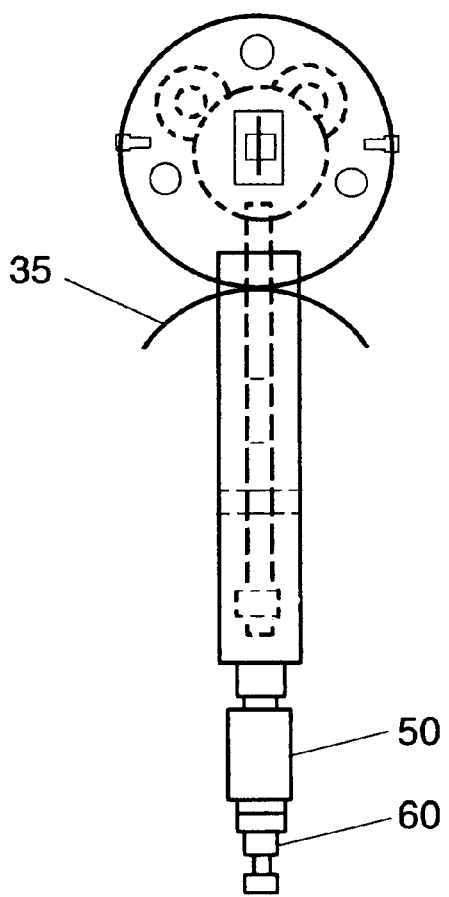
FIG. 5 is an end view of the device.

FIG. 5 is an end view, which shows in profile an optional rest plate 35.

Figure 6:
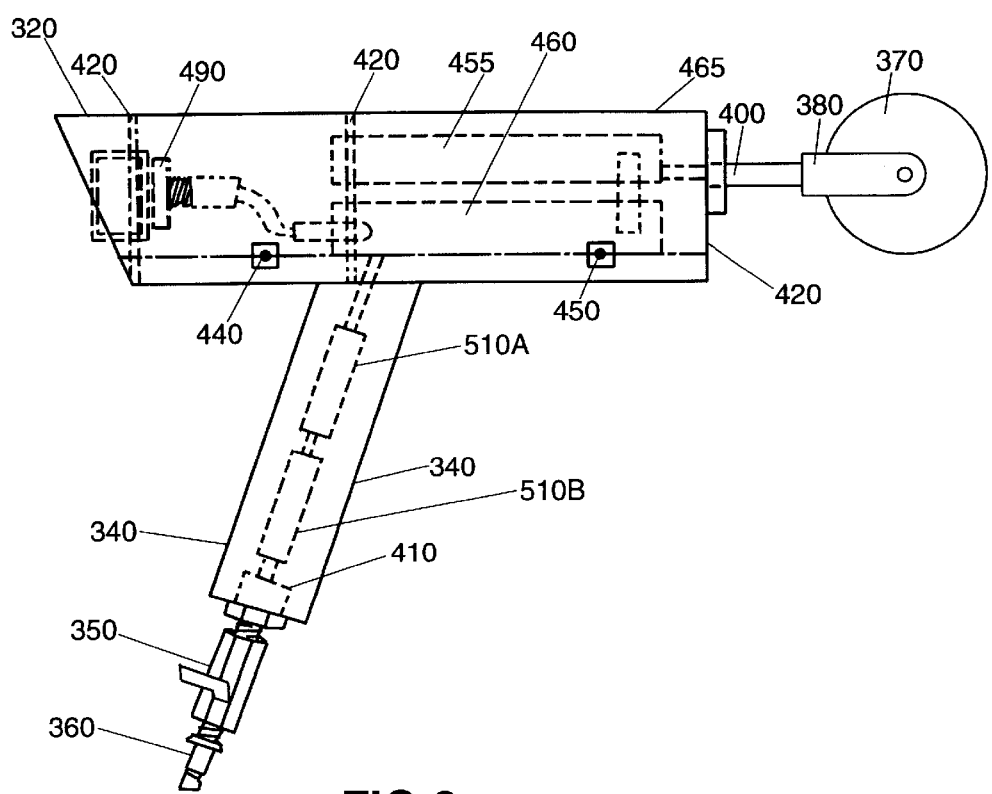
FIG. 6 is a side view revealing the contents of the device.

FIG. 6 shows another embodiment of the invention, one that has a combined armature and handle 340. This illustrates that the angle of the handle 340 with the cylinder 320 can be varied to any comfortable angle. This embodiment has the same cylindrical shape, although the cross section can be varied to an oval, rectangular and other configuration. The back end of the cylinder 320 is shaped like a hood to keep sunlight from the pressure gauge 490. In this embodiment, there are only two pistons 455, 460. It is indicated that there is a hinge 465, which runs along the length of the cylinder. In one embodiment, the hinge 465 is a piano hinge; alternately there can be two or more hinges.

Figure 7:
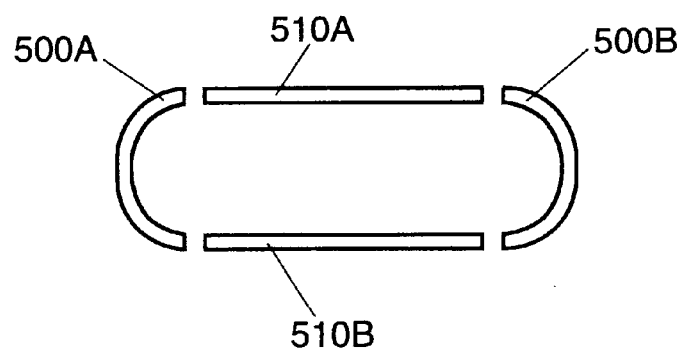
FIG. 7 is a cross-sectional view of the handle 340 shown in FIG. 6.

FIG. 7 shows a cross section of handle 340, indicating the handle can be oval, consisting of two half cylinders 500*a*, 500*b* welded to two plates 510*a*, 510*b*. The handle cross section can also be square or any other convenient shape.

Figure 8:
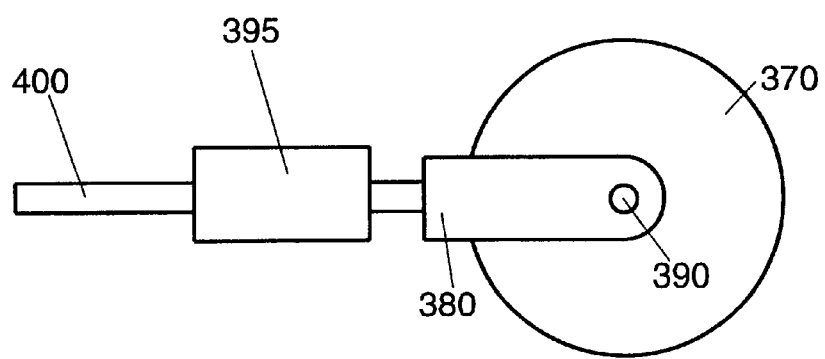
FIG. 8 is an expanded view of the wheel assembly, which also includes a quick disconnect feature.

FIG. 8 shows more detail of the wheel section. In this embodiment, there is a wheel 370, a wheel bracket 380, a solid pin and a plunger shaft 400. This embodiment differs as the wheel assembly also has a quick-disconnect 395 for removing the wheel assembly from the plunger shaft 400. The quick disconnect may be a screw or other male-female tight connection. This permits ease of exchanging the wheel assembly for a wheel of another thickness, which is compatible with the bead width to be tested.

The device may also comprise an applied force compensation system comprising any means known to the art of mechanical or electrical design which passively or actively compensates for force applied by the user. Alternatively the applied force compensation system could be a second strain gauge system dedicated to the measurement of user-applied force. The system may also incorporate an internal computer-controlled feedback mechanism, which measures the user's applied force and adjusts the value of the measured output or limits the range at which testing may occur. Other systems known to the art to ensure that the measured value remains within acceptable accuracy may also be utilized.

FIGS. 9–14 show various schematics of the way in which the compressed air can be routed to maintain pressure in the air chamber, so that a constant pressure is exerted on the probe testing the adhesion of the bead of sealant. These are meant to be representative of several ways to connect the various chambers and are not to be limiting of the invention, which is defined in the claims.

Figure 9:
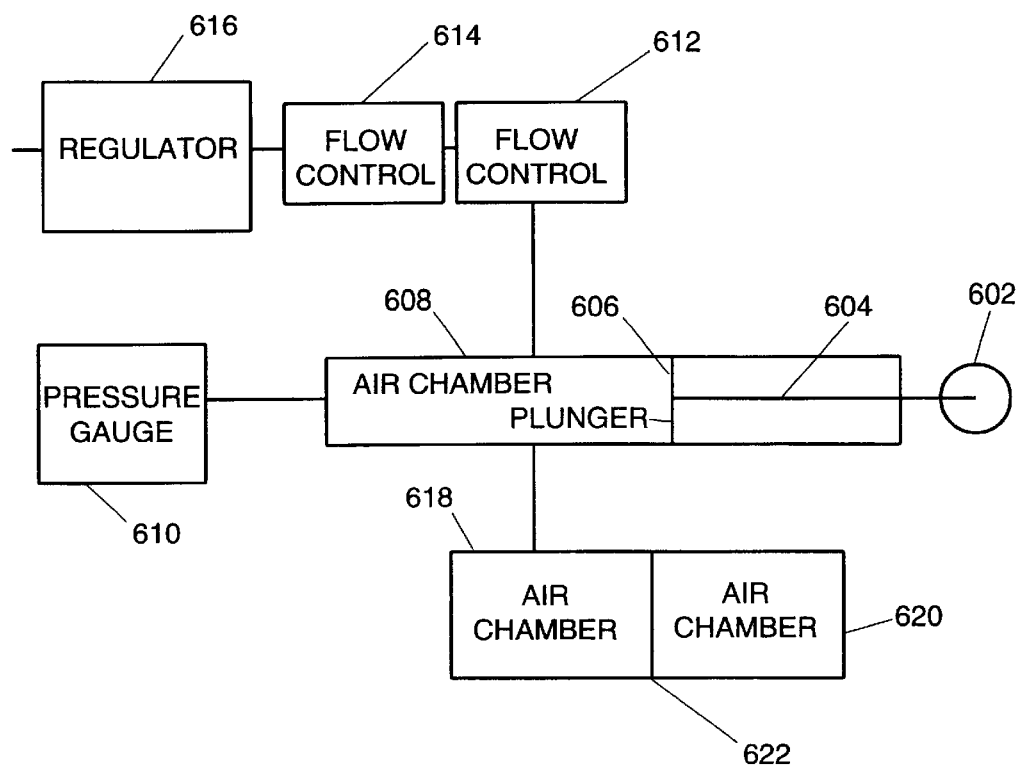
FIG. 9 is a schematic showing one embodiment of the connections of the device.

FIG. 9 shows another embodiment of the device. Like FIG. 2, this device has a wheel 602 attached to plunger shaft 604, which in turn is attached to plunger 606. The air chamber 608 maintains a uniform pressure on the plunger 606, which can be determined from pressure gauge 610. Also connected to the air chamber 608 are two flow controls 612 and 614 arranged in series with the regulator 616, which down-regulates the pressure of the compressed air source (not shown). A second air chamber 618 is connected to the first air chamber 608. Plunger 622 separates the second air chamber 618 from the third air chamber 620. Connecting the first air chamber 608 with the second and third air chambers 618, 620 increases the steadiness of the pressure within the first air chamber 608, which helps maintain even pressure on the plunger 606 which moves the plunger shaft 604 and maintains steady pressure on the wheel 602.

Figure 10:
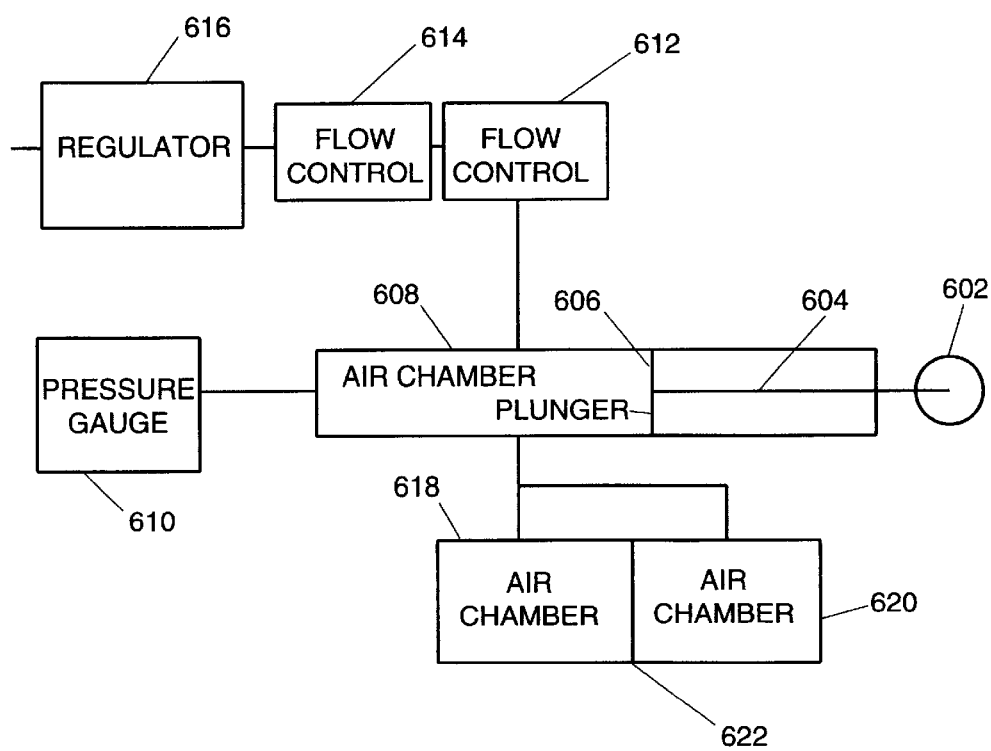
FIG. 10 is a schematic showing one embodiment of the connections of the device.

FIG. 10 shows another embodiment similar to FIG. 9 and hence the above description for FIG. 9 is incorporated in this discussion of FIG. 10. The second and third air chambers 618, 620 are connected in parallel to the first air chamber 608.

Figure 11:
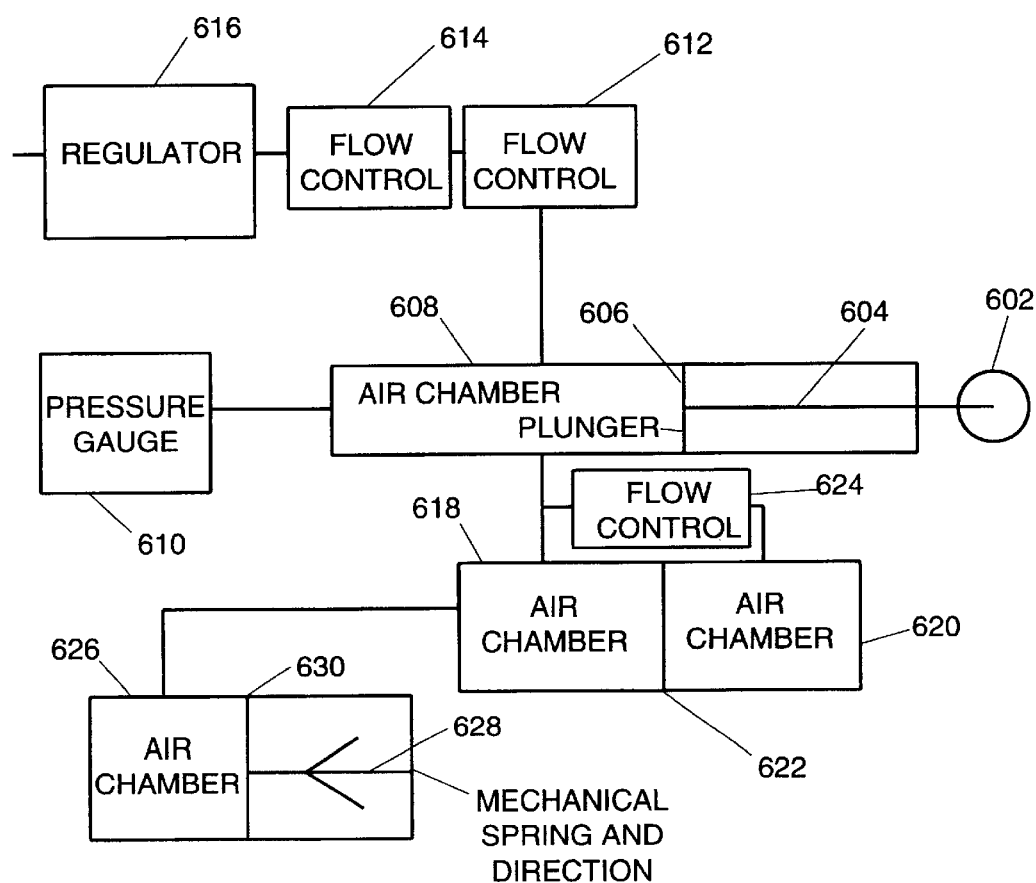
FIG. 11 is a schematic showing one embodiment of the connections of the device and an additional air chamber.

FIG. 11 is another embodiment similar to FIG. 10 and hence the above description for FIG. 10 is incorporated in this discussion of FIG. 11. There is a third flow control 624 between the third air chamber 620 and the first air chamber 608. Also, there is a fourth air chamber 626 whose pressure is maintained by a mechanical spring 628 putting pressure on a plunger 630.

Figure 12:
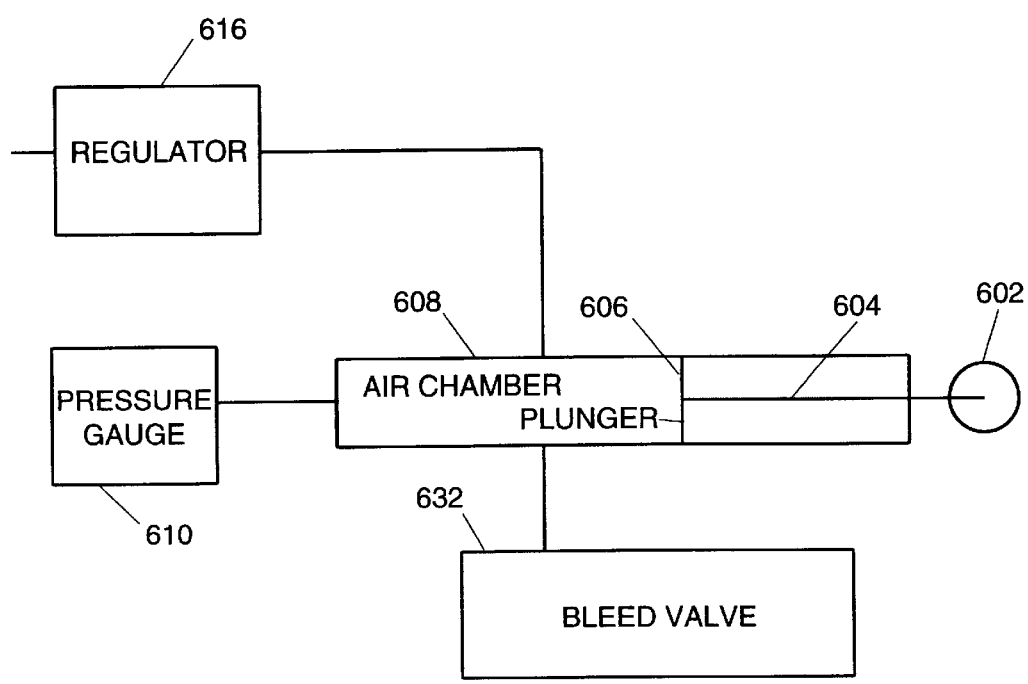
FIG. 12 is a schematic showing one embodiment of the connections of the device and a bleed valve.

FIG. 12 is yet another embodiment similar to FIG. 9 in that it also has a wheel 602, plunger shaft 604, plunger 606, air chamber 608, pressure gauge 610 and regulator 616. The discussion of FIG. 9 is incorporated in this discussion of FIG. 12. However, this embodiment utilizes a bleed valve 632 to help maintain a constant pressure.

Figure 13:
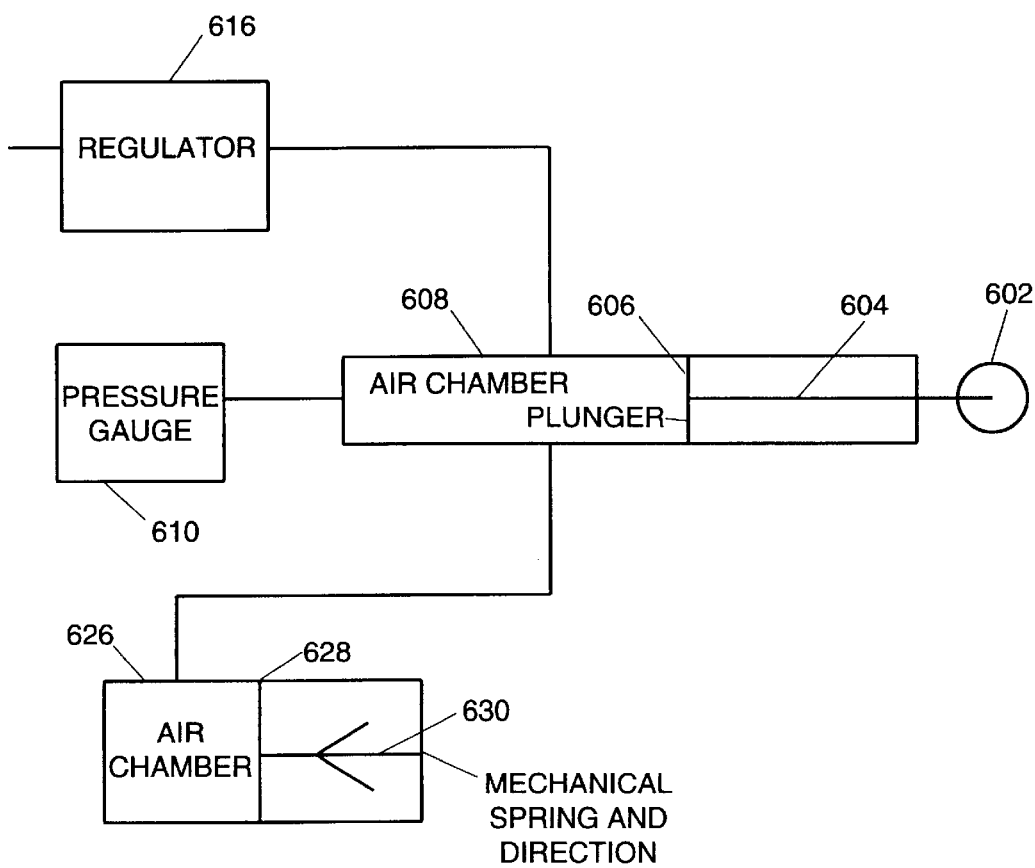
FIG. 13 is a schematic showing one embodiment of the connections of the device and a second air chamber pressurized by an adjustable mechanical spring.

FIG. 13 is similar to FIG. 12, in that it also has a wheel 602, plunger shaft 604, plunger 606, air chamber 608, pressure gauge 610 and regulator 616. The discussion of FIG. 12 is incorporated in this discussion to the extent it does not contradict this discussion. This embodiment utilizes a second air chamber 626 connected to the first air chamber 608. Pressure is maintained in the second air chamber 626 by a plunger 628, which is pressed by an adjustable mechanical spring 630. This embodiment tends to lose less pressurized air than does the embodiment of FIG. 12.

Figure 14:
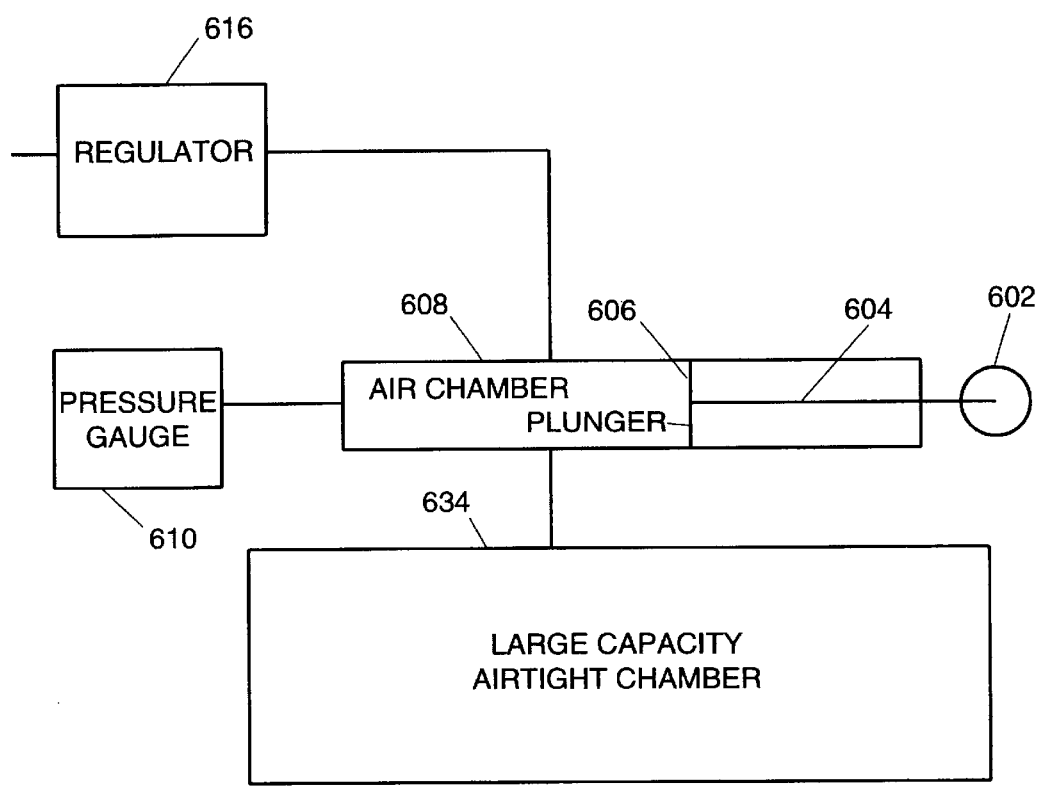
FIG. 14 is a schematic showing one embodiment of the connections of the device with a second large-capacity, airtight chamber.

FIG. 14 is like FIG. 12, in that it also has a wheel probe 602, plunger shaft 604, plunger 606, air chamber 608, pressure gauge 610 and regulator 616. The discussion of FIG. 12 is incorporated herein. In addition, this embodiment has a second, large-capacity air chamber 634 in communication with the first airtight chamber 608 to help maintain pressure therein. This larger reservoir can be a donut shaped cylinder and can be fitted inside the cylinder 20 of FIG. 1. Generally, this system also has a one-way valve (not shown) to bleed pressurized gas and maintain the temperature of the device.

Figure 15:
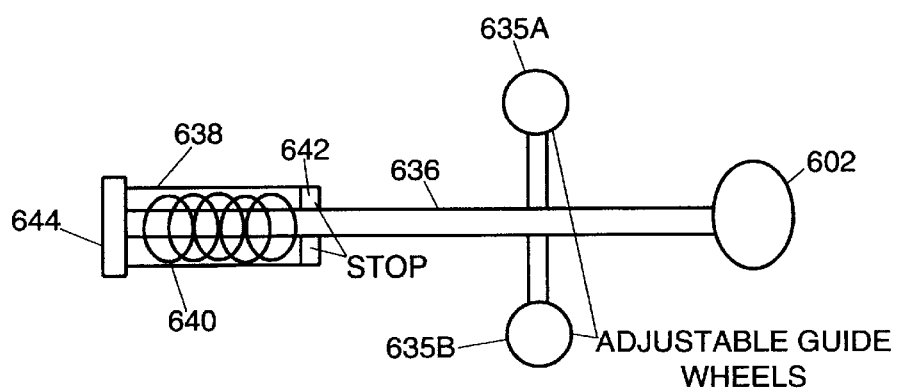
FIG. 15 is a schematic showing a different embodiment of the device, in which the constant pressure is supplied by a spring assembly.

FIG. 15 is yet another embodiment; however, it has no air chambers. This embodiment has a wheel or probe 602 and adjustable guide wheels 635a and 635b, which help provide an even pressure to be exerted by the probe 602 onto the sealant bead (not shown). The wheel 602 connects by way of a piston 636, which enters a housing 638 and contacts a spring assembly 640 to maintain a constant pressure on the wheel 602. The two adjustable guide wheels 635a, 635b are adjusted to the appropriate position to allow an even pressure to be exerted by the probe 602 into the sealant bead while the handle 644 is used to compress the spring assembly 640 and therefore the piston 636. The guide wheels slide up and down the piston until engaging the stop 642 at the bottom of the spring assembly 640. Marks showing calibration positions (not shown) are on the piston 636. The spring assembly 640 can contain one or a plurality of springs. Springs of different weights can be used with sealants of different elongation properties or hardness on the Shore A Durometer scale.

Figure 16:
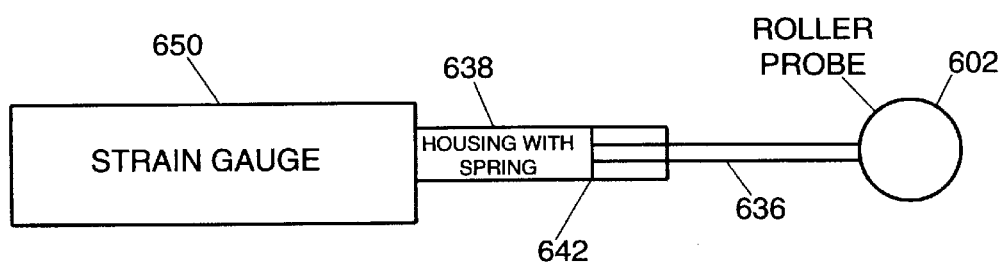
FIG. 16 is a schematic similar to FIG. 15, in which constant pressure is supplied by a spring and pressure can be checked with a strain gauge.

FIG. 16 is an embodiment similar to FIG. 15, but it has no guide wheels. The device has a roller probe 602, piston 636, housing with spring 638 and a stop 642. A strain gauge 650 is incorporated so that the user can target a specific pressure and maintain it by visually monitoring the gauge. The pressure targeted is keyed to the amount of strain required to elongate the sealant bead in the same manner and form as described in Example 1. The primary difference is the need to monitor the gauge 650, and the fact that the pressure developed on the probe 602 is produced by compressing the spring in the housing 638.

EXAMPLE 1

The following describes the procedure used to calibrate the device. The term "passes" as used herein refers to the engagement of the device with a sealant bead (specimen), creating strain resulting in deflection of the bead. The entire bead length is contacted with the device during a pass. Three dial indicators were spaced evenly along the bead to record the bead deflection created by the device in hundredths of an inch at the center of the bead.

Three brands of silicone sealants were studied. Silicone sealants were chosen because of their ability to maintain elastomeric characteristics at variable temperatures. All three sealants have an advertised movement capability of ±50%. Specimens were about 20 inches long and were tested in three different cross sections: 500×250 mils, 750×375 mils and 1000×375 mils. For two sealant brands four colors were tested to observe batch and pigmentation variables. For the third brand, two colors were tested. Three dial indicators were observed for each specimen. Additionally seven different pressures were used to strain each specimen. Five passes were taken for each of the variations. Three target deflections were 50%, 75% and 100% of advertised elongation of each sealant. For example, a one-inch bead with a 50% movement capability would be calibrated to deflections of 250 mils (50% of the movement capability), 375 mils (75%) and 500 mils (100%). Substrate deflection was controlled with a substrate pass, with the substrate deflection recorded, and any deflection of the substrate being deducted from the sealant pass.

Sealant "A" was studied with two specimens per joint width, three joint widths, seven pressures, five passes and three dial indicator readings for a total of 630 recorded deflections. Sealants "B" and "C" were each studied with four specimens per joint width, three joint widths, seven pressures, five passes and three dial indicator readings, for a total of 1260 deflections each.

All tested sealants were neutral-curing silicones with an advertised movement capability of 50%. The data collected for each sealant was used to produce the following tables for sealants, as well as a table showing the average for the three sealants. Data in the tables are in pounds per square inch (PSI).

|  | 500 mils | 750 mils | 1000 mils |
| --- | --- | --- | --- |
| Sealant A (average of 2) D-35 | | | |
| Target 50% | 27.5 | 34.8 | 25.2 |
| Target 75% | 37.2 | 46.8 | 34.8 |
| Target 100% | 50.4 | 60 | 55.2 |
| Sealant B (average of 4) D-28 | | | |
| Target 50% | 24 | 19.2 | 13.2 |
| Target 75% | 33 | 30.6 | 23.4 |
| Target 100% | 43.8 | 49.8 | 37.2 |
| Sealant C (average of 4) D-21 | | | |
| Target 50% | 12.6 | 16.2 | 10.8 |
| Target 75% | 19.8 | 26.4 | 18.6 |
| Target 100% | 30 | 39 | 31.2 |
| Mean (average of all three sealants) D-28 | | | |
| Target 50% | 21.6 | 23.4 | 16.2 |
| Target 75% | 30 | 34.8 | 25.8 |
| Target 100% | 41.4 | 49.8 | 41.4 |

One calibrates the device for a particular brand of sealant and for the bead width. For example, if sealant A was applied in 750 mil width, one would go to the Sealant A table and the column for the 750 mil width. To operate the device to test at 50% target, one would set the device at 34.8 PSI by adjusting the flow control from the pressurized air source, for example, by adjusting the regulator, the flow valve, and bleed valves.

Movement capability and characteristics varied from sealant to sealant and among the colors. Sealant A samples were packaged as medium and low modulus; however, the movement characteristics were nearly identical. Packaging included off-white and dark-brown colors. Pigmentation produced no discernible differences in deflection. Sealant B samples were labeled as medium modulus and came in four colors. Movement capability and hardness varied with the color. Resistance to deflection increased as the maximum movement capability was reached. Sealant C samples were labeled as medium modulus and came in four colors. Movement capability and hardness varied with the color. Resistance to deflection increased slightly as maximum movement capability was reached. Adhesion deteriorated after repeated maximum passes of the device produced adhesive fatigue.

EXAMPLE 2

An evaluation of the weatherproofing sealant joints of a building was performed. The device's internal pressure was chosen to provide a percentage of strain during the evaluation of 75% of the published 50% elongation, or in other words, a 37.5% elongation strain. Locations on the north and south walls of the building were evaluated. The device helped identify three types of failures: adhesion, cohesion and compatibility. Adhesive problems were found to result from these three factors: improper tooling, improperly prepared substrates and insufficient substrate bite. Cohesive problems appeared to result from inadequate sealant depth at the center of the bead in the pre-cast-to-pre-cast joints, where the depth was only about 1/32 of an inch or less. Incompatibility occurred where butyl sealant had been applied to window frames. Frequency of sealant failure occurred at the average rate of 19 per 25-foot section of the eleven-story building. The areas affected ranged in size from small holes to bead lengths up to four inches. In addition, four window sills were found to be totally unsealed.

Although the description above contains many specifics, these should not be construed as limiting the scope of the invention but merely providing illustrations of some of the presently preferred embodiments of this invention. Thus the scope of the invention should be determined by the appended claims and their legal equivalents, rather than by the examples given.

What is claimed is:

1. A device for determining the adequacy of a sealant between construction elements, the device being attached to a source of compressed air whose pressure is controlled by a regulator, the device comprising:

a. a cylinder containing at least one piston, the piston containing an air chamber and a plunger, the air chamber being in communication with a pressure gauge;

b. an armature having a first and a second end, the first end being attached to the cylinder, the second end having a flow valve and an air fitting in communication with the air source, the handle containing tubing as a means to conduct air from the compressed air source, the tubing being interrupted with a bleed valve; and c. a moveable tip such that the tip moves in the direction parallel to the axis of the cylinder, said tip comprising a wheel, a wheel bracket and a plunger shaft, the plunger shaft being attached to the plunger within the piston;

whereby the operator holds the device so that the moveable tip presses against the sealant with constant pressure.

2. The device of claim 1 wherein the moveable tip is removable.

3. The device of claim 1 wherein the pressure gauge is visible when the device is in operation.

4. The device of claim 1 wherein the handle contains two bleed valves replaced with a rounded tip.

5. A method of field testing the adequacy of sealant between two Adjacent materials which are the same or different, the method comprising:

a. providing a bead of sealant between two materials;

b. permitting the sealant to cure;

c. providing a device which is capable of exerting a constant pressure on the sealant and for which the pressure can be adjusted;

d. applying the device to the bead at a variety of pressures to establish an optimal pressure to test the sealant in the field;

e. applying the device with the optimal pressure to the sealant in the field; and f. observing for any separation of the sealant from the materials and any indentation of the sealant.

* * * * *